United States Patent [19]

Bemis

[11] Patent Number: 4,736,860
[45] Date of Patent: Apr. 12, 1988

[54] SHARPS DISPOSAL CONTAINER

[75] Inventor: Richard A. Bemis, Sheboygan, Wis.

[73] Assignee: Bemis Manufacturing Company, Sheboygan Falls, Wis.

[21] Appl. No.: 40,430

[22] Filed: Apr. 20, 1987

[51] Int. Cl.⁴ ............................................. B65D 90/00
[52] U.S. Cl. ................................. 220/1 T; 220/252; 220/18
[58] Field of Search .......................... 220/1 T, 252, 18

[56] References Cited

U.S. PATENT DOCUMENTS 1,333,051 3/1920 Young .................................. 220/252
4,577,563 3/1986 Sidher .................................. 220/18
4,580,688 4/1986 Harris et al. ........................ 220/1 T Primary Examiner—George T. Hall
Attorney, Agent, or Firm—Michael, Best & Friedrich

[57] ABSTRACT

A sharps container apparatus comprising a container including a door manually movable between a closed position and an open position, and a rubber band for biasing the door toward the closed position, the container being compltetly closed when the door is in the closed position, a bracket adapted to be securely mounted on a wall, and interengaging projections and slots on the bracket and on the container for securing the container to the bracket.

11 Claims, 2 Drawing Sheets

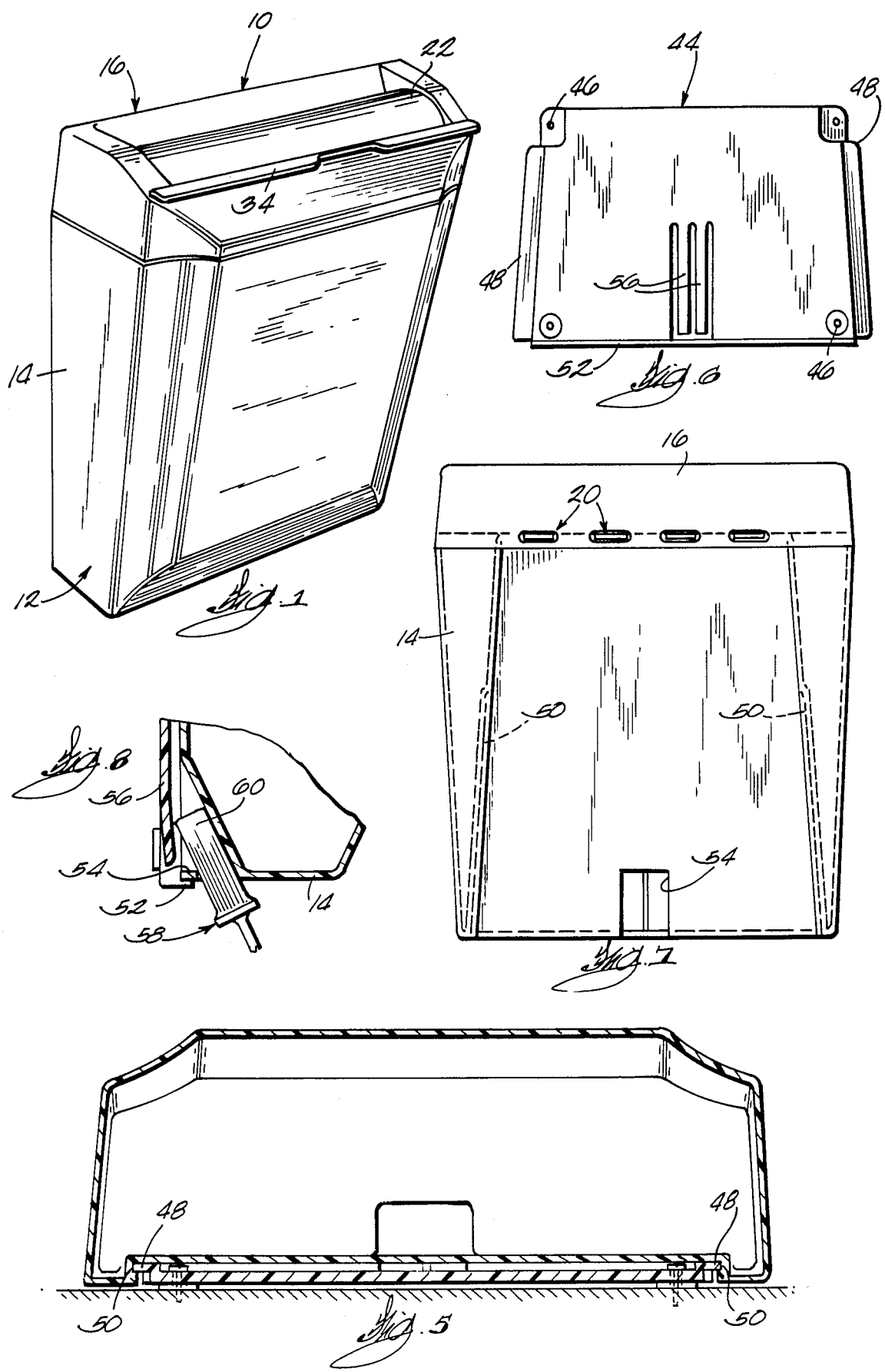

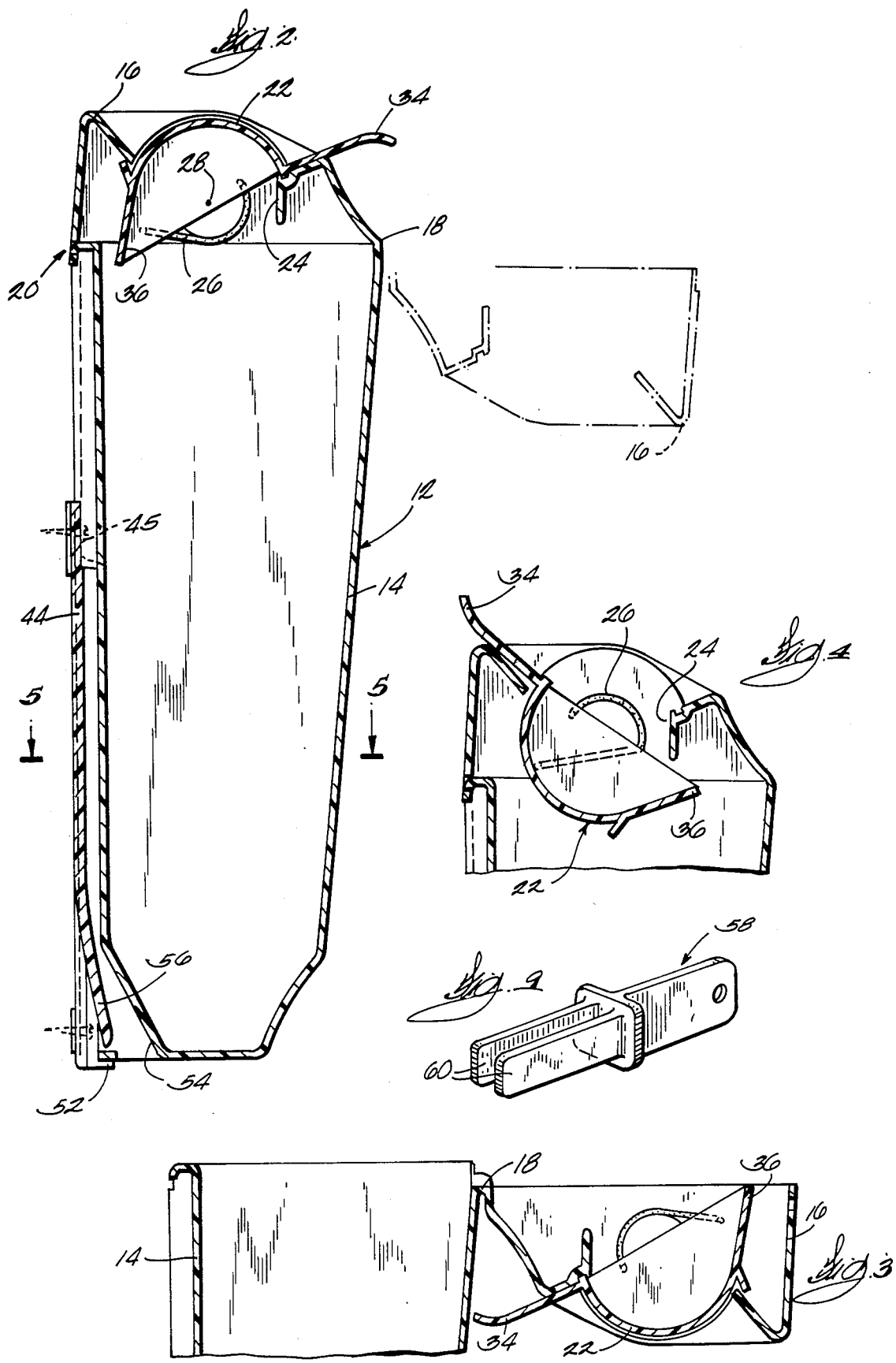

4,736,860

SHARPS DISPOSAL CONTAINER

BACKGROUND OF THE INVENTION

The invention relates to sharps disposal apparatus, i.e., apparatus used in hospitals for containing sharp items such as used hypodermic needles.

Various government agencies recommend or require that hospitals provide a sharps disposal unit in each patient room. These units are intended to prevent used sharp items from causing injury to or infecting patients and hospital personnel and to prevent patients from stealing these items. Theft of used hypodermic needles (typically by intravenous drug users) is becoming a matter of great concern because of the rapid spread of AIDS. On the other hand, there is currently an emphasis in hospitals to make patient rooms more comfortable by improving their appearance and minimizing the amount of medical equipment therein.

Furthermore, government regulations require that some terminal treatment be applied to contaminated waste prior to disposal. In the case of sharps disposal units, this generally means incineration or steam sterilization.

SUMMARY OF THE INVENTION

The invention provides a sharps disposal unit that is easy to manufacture and assemble, is easily removed by authorized personnel but resists unauthorized tampering, is easy to use, has a pleasant appearance, and can be steam sterilized.

More particularly, the invention provides an apparatus comprising a container including a base and a cover connected to the base by an integral hinge. The cover is originally open so that the container can be nested with another container for shipping. The base and the cover include permanently interlocking means so that the container can be permanently closed after shipping.

The cover, which forms the upper portion of the container, includes a door which is manually movable between a closed position and an open position and which is biased toward the closed position. The container is completely closed when the door is in the closed position. Preferably, the door can be opened with one hand holding an object, e.g., a used hypodermic syringe, to be placed in the container.

Additionally, the apparatus comprises means for preventing removal of the contents of the container when the door is in the open position. Thus, the door can be opened to permit insertion of additional contents, but not to remove the present contents. Furthermore, the apparatus comprises means for selectively and permanently locking the door in the closed position when the container is full. In the preferred embodiment, this means includes a pin which is inserted through the container and into the door to prevent movement of the door relative to the container.

The apparatus further comprises a bracket that can be securely mounted on a wall by screws or other suitable means. The sides of the bracket extend generally vertically and slide into complementary slots formed on the back of the container. To attach the container to the bracket, the container is located above the bracket with the sides of the bracket aligned with the slots and is then lowered onto the bracket so that the sides of the bracket slide into the slots.

The bracket and container also include means for preventing unauthorized removal of the container from the bracket and for permitting authorized removal of the container from the bracket. Preferably, this preventing means includes, on the bracket, a resilient projection which is normally in a securing position and which is deflectible to a releasing position. The projection is in the securing position and extends into a recess in the container when the container is secured on the bracket. The preventing means also includes key means for deflecting the projection from the securing position to the releasing position. When the container is secured on the bracket, the projection prevents removal of the container from the bracket unless the key means is used to deflect the projection to the releasing position.

Preferably, the container, the bracket, and the door are all molded in one piece by conventional plastic injection methods. Each piece is molded with a simple two-piece mold that requires no cores or moving parts. The pieces snap together so that no tools are required for assembly. Also, the pieces are made of a plastic that is suitable for steam sterilization.

Other features and advantages of the invention will become apparent to those skilled in the art upon review of the following detailed description and claims.

DESCRIPTION OF THE DRAWINGS

FIG. 1 is a perspective view of an apparatus embodying the invention.

FIG. 2 is a vertical cross sectional view of the apparatus with the door and cover closed.

FIG. 3 is a partial view similar to FIG. 2 with the cover open and the door closed.

FIG. 4 is a partial view similar to FIG. 2 with the cover closed and the door open.

FIG. 5 is a cross-sectional view taken along line 5—5 in FIG. 2.

FIG. 6 is a front elevational view of the bracket.

FIG. 7 is a rear elevational view of the container.

FIG. 8 is a partial view similar to FIG. 2 showing the key releasing the container.

FIG. 9 is a perspective view of the key.

Before one embodiment of the invention is explained in detail, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

An apparatus 10 embodying the ihvention is illustrated in the drawings. As shown in FIGS. 1 and 2, the apparatus 10 comprises a container 12 including a base 14, and a cover 16 connected to the base 14 by an integral hinge 18. The cover 16 is movable relative to the base 14 between an open position (FIG. 3) and a closed position (FIGS. 1, 2 and 4). In order to save space for shipping, the container 12 can be nested with other containers when the cover 16 is in the open position.

The container 12 further includes means for selectively and permanently securing the cover 16 in the closed position, so that the cover 16 cannot be opened once it is closed. While various suitable means can be employed, in the preferred embodiment, this means includes integral, non-reversible snap fasteners 20 on the base 14 and on the cover 16.

The container 12 further includes a door 22 which is located adjacent an opening 24 in the cover 16, which is manually movable between a closed position (FIGS. 1, 2, and 3) and an open position (FIG. 4), and which is biased toward the closed position. The container 12 is completely closed when the cover 16 is in its closed position and the door 22 is in its closed position. While various suitable means can be used for biasing the door 22 toward the closed position, in the illustrated construction, such means includes a rubber band 26 connected between the cover 16 and the door 22.

As best shown in FIG. 2, the door 22 is partially cylindrical and is mounted in the cover 16, for rotation relative thereto about a generally horizontal axis 28, by oppositely extending projections which extend along the axis 28 and which are received in blind bores in the cover 16. The door 22 has thereon a fin 34 which limits pivotal movement of the door 22 beyond the closed position (counterclockwise in FIG. 2) and which facilitates manual movement of the door 22 from the closed position to the open position. Furthermore, the fin 34 allows the door 22 to be opened with one hand holding an object, e.g., a hypodermic needle, to be placed in the container 12.

The apparatus 10 further comprises means for preventing removal of the contents of the container 12 when the door 22 is in the open position. While various suitable means can be employed, in the preferred embodiment, this means includes an integral baffle 36 on the door 22. When the door 22 is moved to the open position, the baffle 36 moves into a position blocking the opening 24 in the cover 16, and the door 22 and baffle 36 form an upwardly opening "cradle" into which an object can be placed. The object is dumped out of the "cradle" when the door 22 returns to the closed position.

In order to prevent the escape of the contents of the container 12 when the container 12 is full, the apparatus 10 further comprises means for selectively and permanently locking the door 22 in the closed position. While various suitable means can be used, in the illustrated construction, such means includes a pin which is insertable through an aperture in the cover 16 and into an aperture or recess in the door 22 when the door 22 is in the closed position. The pin snaps into the cover 16 and the head of the pin fits snugly into a recess or counterbore in the cover 16 so that the pin is not removable once it is fully inserted.

The apparatus 10 further comprises a bracket 44 adapted to be securely mounted on a wall by screws or other suitable means. Preferably, screws 45 are inserted through apertures 46 in the 10 bracket 44. The sides of the bracket 44 extend generally vertically and have thereon integral, forwardly offset tabs or projections 48. As shown in FIG. 6, the tabs 48 converge slightly toward their upper ends.

The apparatus 10 further comprises interengaging means on the bracket 44 and on the container 12 for securing the container 12 to the bracket 44. While various suitable means can be employed, in the preferred embodiment, such means includes, on the bracket 44, the tabs 48, and, on the container 12, a pair of integral slots 50 positioned so as to slidably receive the tabs 48. As shown in FIG. 7, the slots 50 converge in the same manner as the tabs 48, so that the lower ends of the slots 50 are slightly farther apart than are the upper ends of the tabs 48. The container 12 is mounted on the bracket 44 by holding the container 12 above the bracket 44, aligning the slots 50 with the tabs 48, and lowering the container 12 onto the bracket 44 so that the tabs 48 slide into the slots 50. Because the lower ends of the slots 50 are farther apart than the upper ends of the tabs 48, it is easy to align the tabs 48 and the slots 50. Downward movement of the container 12 relative to the bracket 44 is limited by a lip 52 on the lower end of the bracket 44.

The apparatus 10 further comprises means for preventing unauthorized removal of the container 12 from the bracket 44 and for permitting authorized removal of the container 12 from the bracket 44. While various suitable means can be used, in the illustrated construction, this means includes a recess 54 in the rear wall of the container 12, and a pair of resilient, downwardly extending projections 56 on the bracket 44. The projections 56 are normally in a securing position (FIG. 2) and are deflectible to a releasing position (FIG. 8). The projections 56 are in the securing position and extend into the recess 54 when the container 12 is secured on the bracket 44, so that the projections 56 prevent upward movement of the container 12. The means for preventing unauthorized removal of the container 12 also includes key means for deflecting the projections 56 from the securing position to the releasing position. In the preferred embodiment, the key means includes a key 58 (FIGS. 8 and 9) having a pair of generally parallel, spaced apart prongs 60 which are insertable through apertures in the base 14 and into engagement with the projections 56 for moving the projections 56 from the securing position to the releasing position. When the projections 56 are in the releasing position, the container 12 can be moved upwardly relative to the bracket 44 and thus removed from the bracket 44.

Various features of the invention are set forth in the following claims.

I claim:

1. A sharps container apparatus comprising a container including a door manually movable between a closed position and an open position, and means for biasing said door toward said closed position, said container being completely closed when said door is in said closed position, a bracket adapted to be securely mounted on a wall, and interengaging means on said bracket and on said container for securing said container to said bracket.

2. An apparatus as set forth in claim 1 wherein said door can be opened with one hand holding an object to be placed in said container.

3. An apparatus as set forth in claim 1 and further comprising means for preventing removal of the contents of said container while permitting the insertion of additional contents when said door is in said open position.

4. An apparatus as set forth in claim 1 and further comprising means for selectively and permanently locking said door in said closed position.

5. An apparatus as set forth in claim 1 and further comprising means for preventing unauthorized removal of said container from said bracket and for permitting authorized removal of said container from said bracket.

6. An apparatus as set forth in claim 5 wherein said means for preventing unauthorized removal includes, in said container, a recess, and, on said bracket, a resilient projection deflectible from a securing position to a releasing position, said projection being in said securing position and extending into said recess to prevent removal of said container from said bracket when said container is secured on said bracket, and key means for deflecting said projection from said securing position to said releasing position.

7. An apparatus as set forth in claim 1 wherein said interengaging means includes a pair of projections on said bracket and a pair of slots in said container.

8. An apparatus as set forth in claim 1 wherein said container includes a base and an integral cover, said cover being movable relative to said base between an open position and a closed position, and said container further including means for selectively and permanently securing said cover in said closed position.

9. An apparatus as set forth in claim 8 wherein said door is located in said cover.

10. A sharps container apparatus comprising a container including a base, a cover integrally connected to said base and movable relative to said base between an open position and a closed position, means for selectively and permanently securing said cover in said closed position, a door located in said cover and manually movable between a closed position and an open position, and means for biasing said door toward said closed position, said container being completely closed when said door is in said closed position, means for preventing removal of the contents of said container while permitting the insertion of additional contents when said door is in said open position, means for selectively and permanently locking said door in said closed position, a bracket adapted to be securely mounted on a wall, interengaging means on said bracket and on said container for securing said container to said bracket, said interengaging means including a pair of projections on said bracket and a pair of slots in said container, and means for preventing unauthorized removal of said container from said bracket and for permitting authorized removal of said container from said bracket, said means for preventing unauthorized removal including, in said container, a recess, and, on said bracket, a resilient projection deflectible from a securing position to a releasing position, said projection being in said securing position and extending into said recess to prevent removal of said container from said bracket when said container is secured on said bracket, and key means for deflecting said projection from said securing position to said releasing position.

11. An apparatus as set forth in claim 10 wherein said door can be opened with one hand holding an object to be placed in said container.

* * * * *